US008158811B2

(12) United States Patent
Charveron et al.

(10) Patent No.: US 8,158,811 B2
(45) Date of Patent: Apr. 17, 2012

(54) UNSATURATED FATTY HYDROXY ACID DERIVATIVES AND THE DERMOCOSMETOLOGIC USE THEREOF

(75) Inventors: Marie Charveron, Toulouse (FR); Roger Tarroux, Toulouse (FR); Pascal Bordat, Mervilla (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 342 days.

(21) Appl. No.: 12/083,688

(22) PCT Filed: Oct. 20, 2006

(86) PCT No.: PCT/EP2006/067641
§ 371 (c)(1),
(2), (4) Date: Nov. 18, 2008

(87) PCT Pub. No.: WO2007/045693
PCT Pub. Date: Apr. 26, 2007

(65) Prior Publication Data
US 2009/0238784 A1  Sep. 24, 2009

(30) Foreign Application Priority Data

Oct. 21, 2005 (FR) ..................................... 05 10792

(51) Int. Cl.
*C07C 59/00* (2006.01)
(52) U.S. Cl. ........................ 554/213; 514/557
(58) Field of Classification Search .................. 554/213; 514/547
See application file for complete search history.

(56) References Cited

U.S. PATENT DOCUMENTS

| 6,514,507 B2 | 2/2003 | Maignan et al. |
| 2002/0028222 A1 | 3/2002 | Afriat |
| 2002/0086041 A1 | 7/2002 | Maignan et al. |
| 2003/0003115 A1 | 1/2003 | Maignan et al. |
| 2004/0204596 A1 | 10/2004 | Potier et al. |
| 2007/0129430 A1 | 6/2007 | Miyata et al. |
| 2008/0281114 A1* | 11/2008 | Frison et al. .................. 554/127 |

FOREIGN PATENT DOCUMENTS

| CN | 1555351 A | 12/2004 |
| EP | 0 568 307 A | 11/1993 |
| EP | 0 632 008 A | 1/1995 |
| EP | 0 989 111 A1 | 3/2000 |
| EP | 1 547 472 A1 | 6/2005 |
| JP | 61-176510 A | 8/1986 |
| JP | 63-317091 A | 12/1988 |
| JP | 10-147514 A | 6/1998 |
| WO | WO 2005/034938 A1 | 4/2005 |

OTHER PUBLICATIONS

Swissman et al., "The Synthesis of Royal Jelly Acid and its Homologs from Cycloalkanones," J. Orq. Chem., Dec. 1964, vol. 29, pp. 3517-3520.*

Villieras Jet al., Tetrahedron Letters. vol. 26. No. 1, pp. 53-56, (1985).*
S. Dolezal et al. Collect. Czech. Chem. Commun., vol. 31, a es 3765-3774, 1966.*
Hanessian, Stephan et al., Canadian Journal of Chemistry, 65(8), pp. 1859-1866 (1987).
Guindon, Y et al., Journal of Organic Chemistry, 59(5), pp. 1166-1178 (1994).
Nishitani, Kiyoshi et al., Chemical & Pharmaceutical Bulletin, 38(1), pp. 28-35 (1990).
Brown, Richard T. et al., Journal of the Chemical Society, Perkin Transactions 1: Organic and Bio-Organic Chemistry, (11), pp. 1633-1637 (1997).
Bartlett, Paul A. et al., Journal of the American Chemical Society, 102 (1), pp. 337-342 (1980).
AN 144:127969 CA; Zhongguo Gonggong Weisheng (2004), 20(10), 1168.
S. Hannessian et al. "Synthesis of carbocycles from ω-substituted α, β-unsaturated esters via radical-induced cyclizations", Can. J. Chem, 1987.
T. Fujisawa et al., "Chemistry Letters", 1982, vol. 11, No. 2, pp. 219-220.
10-hydroxy-2-Decenoic acid, Chemical Abstracts, RN: 131532-29-1, Jan. 18, 1991.
11-hydroxy-2-Undecenoic acid, Chemical Abstracts, RN: 55027-39-9, Nov. 16, 1984.
12-hydroxy-2-Dodecenoic acid, Chemical Abstracts, RN: 20514-63-0, Nov. 16, 1984.
13-hydroxy-2-Tridecenoic acid, Chemical Abstracts, RN: 251987-03-8, Dec. 30, 1999.
7-hydroxy-2-Heptenoic acid, Chemical Abstracts, RN: 66120-17-0, Nov. 16, 1984.
8-hydroxy-2-Octenoic acid, Chemical Abstracts, RN: 68750-26-5, Nov. 16, 1984.
9-hydroxy-2-Nonenoic acid, Chemical Abstracts, RN: 86109-28-6, Nov. 16, 1984.
Zhao, "Determination of 10-HAD in Royal Jelly," Center for Disease Control and Prevention, Maanshan, Anhui Province, People of Republic of China, 2004, Abstract only provided
Smissman et al., "The Synthesis of Royal Jelly Acid and its Homologs from Cycloalkanones," Royal Jelly Acid From Cycloalkanones, Dec. 1964, pp. 3517-3520.

(Continued)

*Primary Examiner* — Deborah D Carr
(74) *Attorney, Agent, or Firm* — Birch, Stewart, Kolasch & Birch, LLP

(57) ABSTRACT

The invention relates to unsaturated fatty hydroxy acid derivatives of formula (I), wherein $R_n$ is independent from each other H or linear or branched alkyl group which contain from 1 to 6 carbon atoms and which are possibly substituted by a halogen atom, in particular a fluorine atom, $R_1$ is H, F, Cl, Br or $CF_3$, R is H or linear or branched alkyl group which contain from 1 to 6 carbon atoms and which are possibly substituted by a halogen atom, in particular a fluorine atom and $3=n=14$. Said derivatives is suitable for producing an anti-radical, anti-inflammatory and antipruritic dermocosmetologic composition and/or for treating keratinisation and pigmentation troubles and/or for improving healing.

21 Claims, No Drawings

OTHER PUBLICATIONS

Lee et al., Heterogeneous Permanganate Oxidations. 5. The Preparation of Aldehydes by Oxidative Cleavage of Carbon-Carbon Double Bonds, J. Org. Chem., 1993, vol. 58, pp. 2918-2919.

Hurd et al., "Ring-Chain Tautomerism of Hydroxy Aldehydes," J. Am. Chem. Soc., vol. 74, pp. 5324-5329, 1968.

Murthy et al., "Kinetics & Mechanism of Acid Bromate Oxidation of Aliphatic, Aralkyl & Alicyclic Ketones," Indian Journal of Chemistry, vol. 28A, Apr. 1989, pp. 288-291.

Plettner et al., "Why Not be a Queen? Regioselectivity in Mandibular Secretions of Honeybee Castes," Journal of Chemical Ecology, vol. 21, No. 7, 1995, pp. 1017-1029.

Janssen et al., "Biology of Disease," Cell and Tissue Responses to Oxidative Damage, vol. 69, No. 3, pp. 261-274, 1993.

Van Der Vliet et al., "Role of Reactive Oxygen Species in Intestinal Disease," Free Radical Biology & Medicine, vol. 12, pp. 499-513, 1992.

Yu, "Cellular Defenses Against Damage From Reactive Oxygen Species," Physiological Reviews, vol. 74, No. 1, Jan. 1994, pp. 139-162.

Steiling et al., "Different Types of ROS-Scavenging Enzymes Are Expressed during Cutaneous Wound Repair," Experimental Cell Research, 247, pp. 484-494, (1999).

Miyachi et al., "Erythema Multiforme: A Possible Pathogenetic Role of Increased Reactive Oxygen Species," J. Clin. Lab. Immunol., 1986, vol. 19, pp. 11-14.

Kress et al., "Effects of oxygen radicals on nociceptive afferents in the rat skin in vitro," Pain, vol. 62, 1995, pp. 87-94.

Suematsu et al., "Visual assessment of oxidative stress by multifunctional digital microfluorography," pp. 83-99, 1995.

Girotti, "Mechanism of Lipid Peroxidation," Journal of Free Radical in Biology & Medicine, vol. 1, pp. 87-95, 1995.

Vessey et al., "Characterization of the Oxidative Stress Initiated in Cultured Human Keratinocytes by Treatment with Peroxides," 1992, pp. 859-863.

Mizutani et al., "Identification of the human sphingolipid C4-hydroxylase, hDES2, and its up-regulation during keratinocyte differentiation," FEBS Letters 563, 2004, pp. 93-97.

Kielar et al., "Adenosine Triphosphate Binding Cassette (ABC) Transporters Are Expressed and Regulated During Terminal Keratinocyte Differentiation: A Potential Role for ABCA7 in Epidermal Lipid Reorganization," ABC Transporters in Keratinocyte Differentiation, vol. 121, No. 3, Sep. 2003, pp. 465-474.

Steinhoff et al., "Proteinase-activated receptor-2 in human skin: tissue distribution and activation of keratinocytes by mast cell tryptase," Exp Dermatol, 1999, vol. 8, pp. 282-294.

Santulli et al., "Evidence for the presence of a protease-activated receptor distinct form the thrombin receptor in human keratinocytes," Proc. Natl. Acad. Sci. USA, vol. 92, Cell Biology, Sep. 1995, pp. 9151-9155.

Seiberg et al., "The Protease-Activated Receptor 2 Regulates Pigmentation via Keratinocyte-Melanocyte Interactions," Exxperimental Cell Research, vol. 254, 2000, pp. 25-32.

Sharlow et al., "The protease-activated receptor-2 upregulates keratinocyte phagocytosis," Journal of Cell Science, vol. 113, 2000, pp. 3093-3102.

Steinhoff et al., "Proteinase Activated Receptor-2 Mediates Itch: A Novel Pathway for Pruritus in Human Skin," The Journal of Neuroscience, Jul. 16, 2003, vol. 23, No. 15, pp. 6176-6180.

Hou et al., "Immunolocalization of protease-activated receptor-2 in skin: receptor activation stimulates interleukin-8 secretion by keratinocytes in vitro," Immunology, 1998, vol. 94, pp. 356-362.

Iwakiri et al., "Human Airway Trypsin-Like Protease Induces PAR-2-Mediated IL-8 Release in *Psoriasis vulgaris*," J. Invest. Dermatol., pp. 937-944, 1998.

* cited by examiner

UNSATURATED FATTY HYDROXY ACID DERIVATIVES AND THE DERMOCOSMETOLOGIC USE THEREOF

This invention relates to novel unsaturated fatty hydroxy acid derivatives and the dermocosmetologic use thereof.

Many saturated fatty hydroxy acids are known and are described in the literature for their cosmetic and pharmacologic properties. For example, the main lipid constituent of Royal Jelly from bees is an unsaturated fatty hydroxy acid, that is hydroxy-10-decene 2(trans)oic acid (Edward E. Smissman et al., 1964. JOU. 29 3517-3520).

Various documents of the current state of the art describe processes for the preparation of unsaturated fatty hydroxy acids and their esters (Lee et al, 1993, J. Org. Chem., Vol. 58, pages 2918-2919; Hurd and Saunders, 1952, J. Am. Chem. Soc., Vol. 74, pages 5324-5328; Krishnamurthy et al., 1989, Indian J. Chem. Sect. A, vol. 28, pages 288-291; Plettner et al., 1995, J. Chem, Ecol., vol. 21, pages 1017-1030).

More particularly, this invention relates to unsaturated fatty hydroxy acid derivatives of general formula (I):

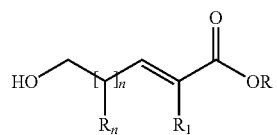

in which:
- $R_n$ independently represents one or other of H or a linear or branched alkyl group consisting of 1 to 6 carbon atoms, possibly substituted by a halogen atom, in particular fluorine.
- $R_1$ represents H, F, Cl, Br, $CF_3$.
- R represents H or a linear or branched alkyl group with 1 to 6 carbon atoms, possibly substituted by a halogen atom, particularly fluorine, and
- $3 \leq n \leq 14$.

According to a particular feature of the invention, unsaturated fatty hydroxy acids of general formula (I) fulfil the following criteria:
- R represents H,
- $R_n$ independently represents one or other of H or a linear or branched alkyl group consisting of 1 to 6 carbon atoms, possibly substituted by a halogen atom, in particular fluorine,
- $R_1$ represents H, F, Cl, Br, $CF_3$.
- $3 \leq n \leq 14$.

on the condition, however, that when $n \neq 10$, at least one of the $R_1$ radicals and $R_n$ radicals does not represent hydrogen.

According to a particular feature of the invention, unsaturated fatty hydroxy acid derivatives of general formula (I) fulfil the following criteria:
- $R_1$ represents F, Cl, Br, $CF_3$,
- $R_n$ independently represents one or other of H or a linear or branched alkyl group consisting of 1 to 6 carbon atoms, possibly substituted by a halogen atom, in particular fluorine,
- R represents H or a linear or branched alkyl group with 1 to 6 carbon atoms, possibly substituted by a halogen atom, in particular fluorine, and
- $3 \leq n \leq 14$.

According to a particular feature of the invention, unsaturated fatty hydroxy acid derivatives of general formula (I) fulfil the following criteria:
- $R_n$ independently represents one or other of H or a linear or branched alkyl group consisting of 1 to 6 carbon atoms, possibly substituted by a halogen atom, in particular fluorine,
- $R_1$ represents H, F, Cl, Br, $CF_3$,
- R represents H or a linear or branched alkyl group with 1 to 6 carbon atoms, possibly substituted by a halogen atom, in particular fluorine, and
- $6 \leq n \leq 14$.

on the condition, however, that when $n \neq 10$, at least one of the $R_1$ radicals and $R_n$ radicals does not represent hydrogen.

According to another particular feature of the invention, unsaturated fatty hydroxy acid derivatives of general formula (I) fulfil the following criteria:
- $R_1 =$ F, Cl, Br, $CF_3$,
- $R_n =$ H, and
- $3 \leq n \leq 14$.

According to another particular feature of the invention, unsaturated fatty hydroxy acid derivatives of general formula (I) fulfil the following criteria:
- $R_1$ represents F, Cl, Br or $CF_3$,
- at least one of the $R_n$ radicals represents a linear or branched alkyl group consisting of 1 to 6 carbon atoms, possibly substituted by a halogen atom, in particular fluorine, and
- $3 \leq n \leq 14$.

According to another particular feature of the invention, unsaturated fatty hydroxy acid derivatives of general formula (I) fulfil the following criteria:
- $R_1 =$ F
- $R_n =$ H
- $3 \leq n \leq 14$.

According to another particular feature of the invention, unsaturated fatty hydroxy acid derivatives of general formula (I) fulfil the following criteria:
- $R_1 =$ F
- $R_n =$ H
- $n = 13$.

According to another particular feature of the invention, unsaturated fatty hydroxy acid derivatives of general formula (I) fulfil the following criteria:
- $R_1 =$ F
- $R_n =$ H
- $n = 6$.

According to another particular feature of the invention, unsaturated fatty hydroxy acid derivatives of general formula (I) fulfil the following criteria:
- $R = R_1 =$ H
- only one of the $R_n$ radicals represents a methyl group, the others being hydrogen atoms, and
- $n = 4$.

According to another particular feature of the invention, unsaturated fatty hydroxy acid derivatives of general formula (I) fulfil the following criteria:
- $R_1 = R_n =$ H and
- $n = 10$.

According to another particular feature of the invention, unsaturated fatty hydroxy acid derivatives of general formula (I) fulfil the following criteria:
- $R_1 =$ F
- $R_n =$ H, and
- $n = 10$.

According to another particular feature of the invention, unsaturated fatty hydroxy acid derivatives of general formula (I) fulfil the following criteria:
- $R_1 =$ F
- $R_n =$ H, and
- $n = 8$.

According to this invention, unsaturated fatty hydroxy acid derivatives of general formula (I) as defined above can be used as active ingredients in combination with a suitable excipient to make up dermocosmetologic compositions with anti-radical, anti-inflammatory, anti-pruriginous activity and/or for use in the treatment of keratinisation and pigmentation disorders and/or for improving healing.

The unsaturated fatty hydroxy acid derivatives of general formula (I) are especially intended for use in compositions intended for the treatment of psoriasis, pruritus and/or atopic dermatitis, as well as for treating skin ageing and white or brown age spots.

According to this invention, unsaturated fatty hydroxy acid derivatives of general formula (I) are more particularly intended for use in compositions aimed at skin whitening.

As a result of their anti-radical activity unsaturated fatty hydroxy acids of general formula (I) are also useful in preventing or limiting the early stages of cutaneous photocarcinogenesis and can therefore be used in the prevention and treatment of various skin tumour disorders.

Unsaturated fatty hydroxy acid derivatives of general formula (I) can be prepared:
by means of the Wittig-Horner reaction by reacting a phosphonate of formula (III)

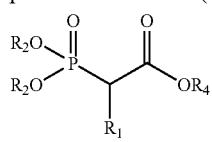

(III)

in which:
$R_1$ is as defined in formula (I);
$R_2$ represents an alkyl group, linear or branched, with 1 to 6 carbon atoms, preferably an ethyl or methyl group, said $R_2$ groups able to form a cyclic structure with oxygen atoms of the $OR_2$ groups and the neighbouring phosphorous atom, and
$R_4$ represents an alkyl group, linear or branched, with 1 to 6 carbon atoms, and is preferably an ethyl group.
or, when $R_1=H$, using the Doebner-Knoevenagel reaction by reacting a malonic acid derivative of formula $R_4OOC—CH_2COOR$, where R is as defined above in formula (I) with a lactol of formula (II):

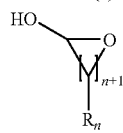

(II)

$R_n$ and n being as defined above,
in order to obtain a hydroxy ester of formula (IV):

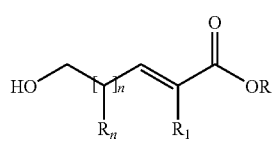

(IV)

in which n, R and $R_1$ are as defined above,
and possibly, when R represents an $R_4$ group as defined above, a saponification reaction of a hydroxy ester of formula (IV) as defined above in order to obtain a corresponding hydroxy acid derivative of formula (I).

This invention is illustrated by the synthesis examples given below:

EXAMPLE 1

Operating Method for the Synthesis of DHA

1. Step 1: Preparation of Oxonan-2-One
43.5 g (345 mmol) of cyclo-octanone is placed in solution in 430 ml of dichloroethane. 170 g (985 mmol) of meta-chloroperbenzoic acid is then added. The medium is heated to 80° C. for 48 hours. At room temperature, 400 ml of a $Na_2S_2O_5$ and $NaHCO_3$ saturated solution (1/1 v/v) are added. The medium is stirred vigorously for 18 hours. The organic phase is separated and contacted with Kl and $H_2O$ for 6 hours. The organic phase is separated and washed with a saturated solution of $Na_2S_2O_3$, a saturated solution of NaCl then dried on $MgSO_4$, filtered and concentrated under vacuum to give 36 g of the crude product.

Lactone is purified by concentration in pentane (60 ml) then by filtration of the meta-chlorobenzoic acid precipitate, w=26.6 g (54%).
The lactone obtained is a compound of formula

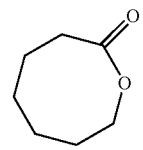

Characterisation
TLC: Rf=0.3 (heptane/ethyl acetate 7/3)
$^1$H NMR (300 MHz, $CDCl_3$): δ 1.42-1.49 (m, 4H), 1.65-1.75 (m, 6H), 2.30 (t, J=5.4 Hz, 2H), 4.30 (t, J=5.7 Hz, 2H).
2. Partial Reduction Step in Lactol
26.6 g (187.2 mmol) of lactone are diluted in 210 ml of toluene under nitrogen. The medium is cooled to −78° C. and 156.4 ml (189.1 mmol) of Dibal-H in solution at a concentration of 20% in toluene are added drop by drop while maintaining the temperature at −78° C. The mixture is stirred for 2 hours at −78° C. 200 ml of a saturated solution of Rozen salts are added at −78° C. After stirring vigorously for 18 hours at room temperature, the biphase mixture is filtered on celite then extracted with ethyl acetate. The organic phases are washed with a saturated NaCl solution, dried on $MgSO_4$, filtered and concentrated under vacuum to give 26 g of the crude product (25% of which is the diol derivative, i.e. an estimated yield of 72%). Lactol, balanced in terms of the open and cyclic forms, is therefore used without further purification.
Characterisation:
TLC: Rf=0.4 (heptane/ethyl acetate 6/4)
$^1$H NMR (300 MHz, $CDCl_3$): δ 1.34-1.68 (m, 10H), 2.45 (t, J=5.4 Hz, 2H), 3.66 (t, J=6.6 Hz, 2H), 9.78 (t, J=1.8 Hz, 1 H).
3. Step 3: Wittig-Horner Reaction.
19 g (131.8 mmol) of lactol are diluted in 250 ml of ethanol. 31.4 ml (158.1 mmol) of triethylphosphonacetate are added to the medium in the presence of 27.3 g (197.5 mmol) of potassium carbonate. The reaction medium is heated to 40° C. for 18 hours. At room temperature, the medium is hydrolysed by 200 ml of distilled water and extracted with ethylacetate. The organic phases are washed with a saturated NaCl solution, dried on $MgSO_4$, filtered and concentrated under vacuum to give 20 g of the crude product.

The ester obtained is purified by chromatography with elution in heptane/ethylacetate 7/3. 15 g of the product is obtained (53% yield). The ester obtained is a compound of formula:

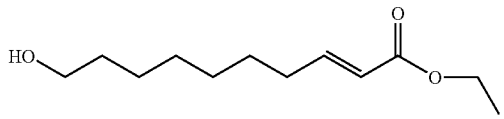

Characterisation:

TLC: Rf=0.4 (heptane/ethyl acetate 7/3)

$^1$H NMR (300 MHz, CDCl$_3$): δ 1.24-1.38 (m, 9H), 1.43-1.50 (m, 2H), 1.51-1.57 (m, 2H), 2.15-2.21 (q, 2H), 3.60-3.64 (t, 2H), 4.14-4.20 (t, 2H), 5.77-5.82 (d, J=15.6 Hz, 1 H), 6.91-6.98 (dt, J=15.6 Hz, 1 H).

4. Step 4: Saponification Reaction.

0.60 g (2.81 mmol) of hydroxy ester is dissolved in 10 volumes of tetrahydrofurane. 3.4 ml (6.75 mmol) of a 2M soda solution are added slowly. The medium is heated to 65° C. for 3 hours. Once the reaction ends, the medium is hydrolysed by adding a 3M hydrochloric acid solution until pH=2 is obtained. The mixture is concentrated to dryness and the aqueous phase is extracted by ethylacetate. The organic phases are washed with a saturated NaCl solution, dried on MgSO$_4$, filtered and concentrated under vacuum to give 0.6 g of the crude product.

The expected unsaturated hydroxy acid derivative is obtained in the form of a white solid by recrystallisation in acetonitrile, w=0.37 g (71%).

The hydroxy acid derivative obtained is a compound of formula

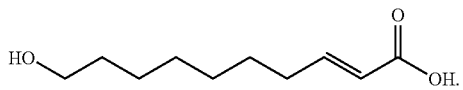

Characterisation:

TLC: Rf=0.1 (heptane/ethyl acetate 6/4)

$^1$H NMR (300 MHz, CDCl$_3$): δ 1.33-1.37 (m, 6H), 1.45-1.49 (m, 2H), 1.55-1.58 (m, 2H), 2.20-2.25 (q, 2H), 3.62-3.66 (t, 2H), 5.79-5.84 (d, J=15.6 Hz, 1 H), 7.03-7.10 (dt, J=15.6 Hz, 1 H).

Mass spectroscopy: [M−Na]$^+$ 209 (calculated 186)

Melting point: 62.5° C.±1° C.

EXAMPLE 2

Operating Procedure for the Synthesis of α-Fluorinated DHA of 10-hydroxy-dec-2-fluoro-2 enoic acid: (R1=F, n=6)

Only step 3 is different: using lactol (0.89 g, 7.7 mmol), the Wittig-Horner reaction is carried out in the presence of methyldiethylphosphonofluoroacetate (2.1 g, 9.2 mmol) and potassium carbonate (1.6 g, 11.5 mmol) in ethanol (9 ml) at 40° C. Step 4 is carried out in accordance with the preceding protocol. The product obtained after recrystallisation is in the form of a cis-trans mixture. The hydroxy acid derivative obtained is a compound of formula:

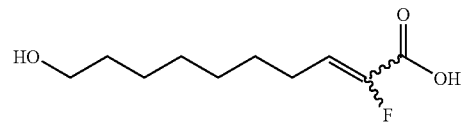

Characterisation:

TLC: Rf=0.1 (heptane/ethyl acetate 6/4)

$^1$H NMR (300 MHz, CDCl$_3$): δ 1.36-1.62 (m, 20H), 2.27-2.30 (m, 2H, cis form), 2.50-2.58 (m, 2H, trans form), 3.69 (m, 4H), 6.05 (dt, J=21.6 Hz, 1 H, trans form) and 6.25 (dt, J=40.8 Hz, 1 H, cis form).

Mass Spectroscopy: [M−Na]$^+$ 227 (calculated 204)

EXAMPLE 3

Operating Procedure for the Synthesis of 9-hydroxy-nona-2t-enoic acid

The protocol for DHA synthesis is applied to cycloheptanone in order to obtain 9-hydroxy-nona-2t-enoic acid.

Characterisation:

TLC: Rf=0.1 (heptane/ethyl acetate 6/4)

$^1$H NMR (300 MHz, CDCl$_3$): δ 1.36-1.61 (m, 8H), 2.22-2.27 (m, 2H), 3.67 (t, J=6.3 Hz, 2H), 5.84 (dt, J=15.6 Hz, 1 H), 7.09 (dt, J=15.6 Hz, 1 H).

Mass Spectroscopy: [M−Na]$^+$ 195 (calculated 172)

EXAMPLE 4

Operating Procedure for the Synthesis of 11-hydroxy-undeca-2t-enoic acid

The protocol for DHA synthesis is applied to cyclononanone in order to obtain 11-hydroxy-undeca-2t-enoic acid.

Characterisation:

TLC: Rf=0.1 (heptane/ethyl acetate 6/4)

$^1$H NMR (300 MHz, CDCl$_3$): δ 1.33-1.61 (m, 12H), 2.20-2.28 (m, 2H), 3.66 (t, J=6.0 Hz, 2H), 5.84 (dt, J=15.9 Hz, 1 H), 7.09 (dt, J=15.9 Hz, 1 H).

Mass Spectroscopy: [M−Na]$^+$ 223 (calculated 200)

EXAMPLE 5

Operating Procedure for the Synthesis of 12-hydroxy-dodeca-2t-enoic acid

The protocol for DHA synthesis is applied to cyclodecanone in order to obtain 12-hydroxy-dodeca-2t-enoic acid.

Characterisation:

TLC: Rf=0.1 (heptane/ethyl acetate 6/4)

$^1$H NMR (300 MHz, CDCl$_3$): δ 1.35-1.56 (m, 14H), 2.20-2.27 (m, 2H), 3.55 (t, J=6.6 Hz, 2H), 5.80 (dt, J=15.6 Hz, 1 H), 6.96 (dt, J=15.6 Hz, 1 H).

Mass Spectroscopy: [M−Na]$^+$ 237 (calculated 214)

EXAMPLE 6

Operating Procedure for the Synthesis of 12-hydroxy-dodeca-2-fluoro-2t-enoic acid The protocol for the synthesis of DHA fluorinated in position 2 (example 2) is applied to cyclodecanone in order to obtain 12-hydroxy-dodeca-2-fluoro-2-enoic acid in the form of a cis/trans mixture.

Characterisation:
    TLC: Rf=0.1 (heptane/ethyl acetate 6/4)
    $^1$H NMR (300 MHz, CDCl$_3$): δ 1.34-1.56 (m, 14H), 2.24-2.27 (m, 2H cis form) or 2.49-2.54 (m, 2H structure trans), 3.55 (t, J=6.6 Hz, 2H), 5.97 (dt, J=21.9 Hz, 1 H structure trans) or 6.10 (dt, J=55.2 Hz, 1 H, cis form).
    Mass Spectroscopy: [M−Na]$^+$ 255 (calculated 232)

EXAMPLE 7

Operating Procedure for the Synthesis of 13-hydroxy-tridec-2t-enoic acid

The protocol for DHA synthesis is applied to oxacyclododecan-2-one in order to obtain 13-hydroxy-tridec-2t-enoic acid.
Characterisation:
    TLC: Rf=0.1 (heptane/ethyl acetate 6/4)
    $^1$H NMR (300 MHz, CDCl$_3$): δ 1.27-1.63 (m, 16H), 2.21-2.28 (m, 2H), 3.64 (t, J=3.6 Hz, 2H), 5.84 (dt, J=15.6 Hz, 1 H), 7.09 (dt, J=15.6 Hz, 1 H).
    Mass Spectroscopy: [M−Na]$^+$ 251 (calculated 228)

EXAMPLE 8

Operating Procedure for the Synthesis of 14-hydroxy-tetradec-2t-enoic acid

The protocol for DHA synthesis is applied to oxacyclotridecan-2-one in order to obtain 14-hydroxy-tetradec-2t-enoic acid.
Characterisation:
    TLC: Rf=0.1 (heptane/ethyl acetate 6/4)
    $^1$H NMR (300 MHz, CDCl$_3$): δ 1.29-1.35 (m, 14H), 1.46-1.61 (m, 4H), 2.21-2.29 (m, 2H), 3.66 (t, J=6.6 Hz, 2H), 5.84 (dt, J=15.6 Hz, 1 H), 7.09 (dt, J=15.6 Hz, 1 H).
    Mass Spectroscopy: [M−Na]$^+$ 265 (calculated 242)

EXAMPLE 9

Operating Procedure for the Synthesis of 14-hydroxy-tetradec-2-fluoro-2-enoic acid The protocol for synthesis of DHA fluorinated in position 2 (example 2) is applied to oxacyclotridecan-2-one in order to obtain 14-hydroxy-tetradec-2-fluoro-2-enoic acid in the form of a cis/trans mixture.
Characterisation:
    TLC: Rf=0.1 (heptane/ethyl acetate 6/4)
    $^1$H NMR (300 MHz, CDCl$_3$): δ 1.29 (m, 28H), 1.42-1.62 (m, 8H), 2.27-2.31 (m, 2H, cis form), 2.51-2.56 (m, 2H, trans form), 3.68 (t, J=6.6 Hz, 2H), 3.70 (t, J=6.6 Hz, 2H), 6.04 (dt, J=21.3 Hz, 1 H, trans form), 6.27 (dt, J=33.0 Hz, 1 H, cis form).
    Mass Spectroscopy: [M−Na]$^+$ 283 (calculated 260)

EXAMPLE 10

Operating Procedure for the Synthesis of 17-hydroxy-heptadec-2t-enoic acid

The protocol for DHA synthesis is applied to cyclopentadecanolide in order to obtain 17-hydroxy-heptadec-2t-enoic acid.
Characterisation:
    TLC: Rf=0.1 (heptane/ethyl acetate 6/4)
    $^1$H NMR (300 MHz, CDCl$_3$): δ 1.27-1.32 (m, 20H), 1.46-1.61 (m, 4H), 2.20-2.29 (m, 2H), 3.67 (t, J=6.6 Hz, 2H), 5.84 (dt, J=15.6 Hz, 1 H), 7.08 (dt, J=15.6 Hz, 1 H).
    Mass Spectroscopy: [M−Na]$^+$ 307 (calculated 284)

EXAMPLE 11

Operating Procedure for the Synthesis of 17-hydroxy-heptadec-2-fluoro-2-enoic acid The protocol for synthesis of DHA fluorinated in position 2 (example 2) is applied to cyclopentadecanolide in order to obtain 17-hydroxy-heptadec-2-fluoro-2-enoic acid in the form of a cis/trans mixture.
Characterisation:
    TLC: Rf=0.1 (heptane/ethyl acetate 6/4)
    $^1$H NMR (300 MHz, CDCl$_3$): δ 1.27 (m, 40H), 1.45-1.62 (m, 8H), 2.24-2.32 (m, 2H, cis form), 2.50-2.58 (m, 2H, trans form), 3.69 (t, J=6.6 Hz, 4H), 6.05 (dt, J=21.6 Hz, 1 H, trans form) et 6.26 (dt, J=40.8 Hz, 1 H, cis form).
    Mass Spectroscopy: [M-H] 301 (calculated 302)
    Melting Point: 77° C.±1° C.

EXAMPLE 12

Operating Procedure for the Synthesis of 18-hydroxy-ocatadec-2t-enoic acid (R1=H, n=14)

The protocol for DHA synthesis is applied to hexacyclodecanolide in order to obtain 18-hydroxy-octadec-2t-enoic acid.
Characterisation:
    TLC: Rf=0.1 (heptane/ethyl acetate 6/4)
    $^1$H NMR (300 MHz, CDCl$_3$): δ 1.27-1.65 (m, 26H), 2.19-2.39 (m, 2H), 3.67 (t, J=6.6 Hz, 2H), 5.83 (dt, J=15.6 Hz, 1 H), 7.09 (dt, J=15.6 Hz, 1 H).
    Mass Spectroscopy: [M−Na]$^+$ 321 (calculated 298)

EXAMPLE 13

Characterisation of 16-hydroxy-hexadec-2t-enoic acid

Characterisation:
    TLC: Rf=0.1 (heptane/ethyl acetate 6/4)
    $^1$H NMR (300 MHz, CDCl$_3$): δ 1.27-1.32 (m, 18H), 1.46-1.61 (m, 4H), 2.21-2.28 (m, 2H), 3.66 (t, J=6.6 Hz, 2H), 5.85 (dt, J=15.6 Hz, 1 H), 7.09 (dt, J=15.6 Hz, 1 H).
    Mass Spectroscopy: [M−Na]$^+$ 293 (calculated 270)
Example of Doebner—Knovenagel Reaction Using Oxacyclotridecanol.

1.4 g (7.0 mmol) of oxacyclotridecanol (obtained by means of the lactol partial reduction protocol) is dissolved under nitrogen in 4 volumes of pyridine in the presence of 1.09 g (10.5 mmol) of malonic acid and 0.11 ml of piperidine. The reaction medium is heated at 80 for 1 h30 then under reflux for 2 h. At room temperature, the solution is poured onto a 3M HCl (50 ml). The filtered solid is washed with water then recrystallised in acetonitrile (1.2 g obtained i.e. 70% yield).

Unsaturated fatty hydroxy acid derivatives according to the invention underwent a number of experiments to demonstrate their benefit as active ingredients in dermatological and/or cosmetic compositions.

Study of the Anti-radical Effect on Activated Oxygen Species (AOS)

In the course of normal cell metabolism, during occasional exposure of the skin to stressful agents or in the course of dermatological diseases, reactive oxygenated species called Activated Oxygen Species (AOS) are produced (Y. M. W. Janssen et al, 1993). AOS described as highly reactive metabolites play an important role in a large number of processes such as inflammation, ageing and tumours.

AOSs are considered to be secondary messengers in cell signalling processes relating to oxidative stress and therefore as precocious mediators of the inflammatory process (A. Van Der Vliet and A. Bast. 1992)

Overproduction of AOSs leads to considerable damage in the cell. Certain cell constituents are therefore major targets of oxidative stress: lipid constituents of the plasma membrane (lipoperoxidation), proteins (denaturation and degradation) and genetic material or DNA (mutations) can undergo alterations. Cells are capable of limiting oxidative damage through various anti-radical defence systems (enzymatic and non-enzymatic antioxidants) (B. P. Yu, 1994; H. Steiling et al, 1999).

Nevertheless, under certain conditions, AOSs are produced in quantities such that cellular antioxidant activity is inadequate. These AOSs therefore become factors which trigger inflammatory disorders and tissue ageing (Y. Miyachi et al, 1986; M. Kress et al, 1995).

There are different chemical (e.g.: $H_2O_2$) or physical (e.g.: UVA) agents capable of generating oxidative stress in vitro. The AOSs produced alter various cell targets (membranes, DNA, or proteins) and this alteration can be analysed using commonly used biological procedures such as TBARS assay for lipid lipoperoxidation or in vitro assay of intracellular AOSs using an $H_2DCF$-DA probe.

We set up an in vitro study model of oxidative stress induced by $H_2O_2$/iron as $H_2O_2$ generates huge amounts of intracellular AOSs as a result of a chain reaction triggered by oxidation of membrane lipids.

This technique is based on the use of a fluorescent probe, 6-carboxy-2',7'-dichlorodihydro fluorescein diacetate, di (acetoxymethyl ester) ($H_2DCF$-DA) which once it penetrates into the cell is deacetylated by intracellular esterases and thus forms $H_2DCF$. This product is oxidized by intracellular AOSs into a highly fluorescent compound: 2',7'-dichlorofluorescein (DCF) (*Suematsu M et al., 1996, Free Radicals Practical Approach, Punchard ed*. P 83-99).

The materials and methods used for in vitro assay of intracellular AOSs are given below.

a) Cell tool
Cutaneous murin fibroblast cell line L929.
b) Materials
96 well flat based microplate.
Cytofluor II cytofluorameter: Ref. PERCEPTIVE BIOSYSTEMS.
c) Reagents
Cell culture reagents:
Dulbecco's Modified Eagle Medium as the culture medium (DMEM)
Foetal calf serum
Phosphate buffer PBS pH 7.4
Trypsin EDTA (1X)
Fluorescent probe
6-carboxy-2',7'-dichlorodihydrofluorescein diacetate, di(acetoxymethyl ester) (PM.675,43)
Cell stimulation products
Hydrogen peroxide ($H_2O_2$) 3% Ref. GIFRER (Gifrer Barbezat Laboratory)
Ferrous ammonium sulphate ($Fe^{2+}$)
Ferric ammonium sulphate ($Fe^{3+}$)

d) Products tested:

The concentrations tested are non cytotoxic concentrations. Cytotoxicity was carried out using the neutral red method after incubation of the product for 3 hours.

The reference anti-radical product is vitamin E or alphatocopherol (MW:430.7) (SIGMA, ref: T-1539)

The stock solution is prepared at a concentration of 400 mg/ml in DMSO and stored at −20° C. The pre-treatment solution is prepared freshly at a concentration of 400 μg/ml in culture medium without foetal calf serum.

For the evaluation of unsaturated fatty hydroxy acid derivatives, the dilutions are prepared in freshly prepared culture medium for a concentration range of 0.02, 0.2, 2 and 20 ng/ml.

e) Protocol.

Cell culturing.

Cells from the fibroblast line L929 were cultured in 96-well flat base microplates in 100 μl of DMEM supplemented with 10% foetal calf serum. These were incubated overnight at 37° C. in a humid atmosphere at 5% $CO_2$. The blank plate without cells was evaluated using 6 wells.

Pre-treatment of Cells:

Dilutions of the products to be tested and reference molecule were made up in culture medium without foetal calf serum then deposited in 7 wells at a rate of 100 μl per well.

Cells were then incubated for 3 hours at 37° C. in a humid atmosphere at 5% $CO_2$.

'Blank' (natural fluorescence of cells), 'control' (basal production of AOS) and 'stimulated' cells (production of AOSs after oxidative treatment) were covered with 100 μl of DMEM.

The 'control' cells were incubated with a probe but were neither pretreated nor treated.

The 'stimulated' cells were incubated with a probe and were treated but not pretreated.

The 'blank' cells were neither pretreated nor incubated with a probe nor treated.

Incubation of Cells with the Probe and Oxidative Stress:

Cells were rinsed in PBS 1X at a rate of 100 μl per well. They were then incubated for 30 minutes at 37° C. in a humid atmosphere at 5% $CO_2$ with 50 μl of the $H_2DCF$-DA probe at 5 μM.

After 30 minutes of contact with the probe alone, cells were incubated for 30 minutes at 37° C. in a humid atmosphere at 5% $CO_2$ with the addition of 25 μl of $H_2O_2$ at 800 μM and 25 μl of ferrous iron and ferric iron solution at 8 mM in order to obtain final concentrations of 200 μM of $H_2O_2$ and 2 mM of ferrous iron and ferric iron.

Cells were then rinsed with PBS 1X at a rate of 100 μl per well then incubated for 30 minutes at 37° C. in a humid atmosphere at 5% $CO_2$ with 100 μl of PBS 1X.

This incubation for 1 h 30 minutes at 37° C. allows intracellular esterases to deacetylate the probe into $H_2DCF$ which can be oxidized by the intracellular AOSs into DCF: a fluorescent compound whose formation is proportional to the quantity of intracellular AOSs.

The intensity of fluorescence is read on a cytofluorimeter at λexcitation=485 nm and λemission=530 nm. This reflects the amount of intracellular AOS produced.

Diagram of the Study Protocol:

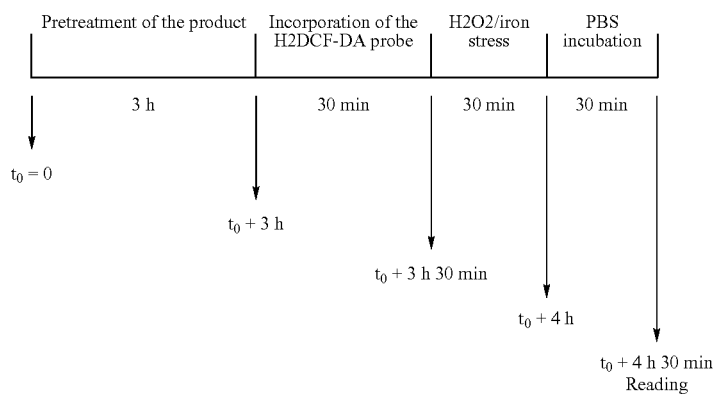

Calculation of % protection against the production of intracellular AOSs.

The ratio below makes it possible to calculate the % protection against the production of intracellular AOSs for each product concentration tested (because the intensity of fluorescence or IF reflects the release of intracellular AOSs)

$$\frac{[\text{IF Oxidant}(H_2O_2/\text{Iron}) - \text{IF}(\text{Oxidant} + \text{Product})] \times 100}{\text{IF Oxidant}(H_2O_2/\text{Iron}) - \text{IF Control}}$$

The values given in the table below are the percentages of inhibition of intracellular AOS production following exogenous oxidative stress compared to 'blank' cells (100%) and 'stimulated' cells (0%).

Mean protection percentages for the 13 molecules tested at the 4 concentrations for line L929 are presented in Table I below.

TABLE I

Analysis of protection against intracellular production of AOSs for 13 molecules derived from unsaturated fatty hydroxy acids:
Percentage inhibition of the intracellular production of AOS.
Vit. E 400 µg/ml 47%

| Compound formula I | | | | Doses | | | |
|---|---|---|---|---|---|---|---|
| n | R | $R_n$ | $R_1$ | 0.02 ng/ml | 0.2 ng/ml | 2 ng/ml | 20 ng/ml |
| 3 | H | H | F | 3 | −3 | −32 | −51 |
| 3 | H | H | H | 21 | 15 | 11 | 14 |
| 4 | H | H | F | 10 | 6 | −4 | −36 |
| 4 | H | H | H | 17 | 9 | 9 | 0 |
| 5 | H | H | H | 56 | 47 | 46 | 36 |
| 6 | H | H | F | 15 | 4 | 5 | −9 |
| 6 | H | H | H | | 33 | | |
| 9 | H | H | H | 9 | 10 | 6 | −22 |
| 10 | H | H | F | 29 | 16 | 0 | −19 |
| 10 | H | H | H | 11 | 4 | −20 | −34 |
| 13 | H | H | F | 36 | 28 | 14 | −9 |
| 13 | H | H | H | 3 | 13 | −1 | −10 |
| 14 | H | H | F | 6 | −17 | −26 | −42 |

Pre-incubation: 3 h
Number of tests=3 for all compounds.
Number of tests=18 for vit. E In vitro at the cellular level, exogenous stress as a result of $H_2O_2/Fe^{2+}/Fe^{3+}$ is capable of triggering the production of intracellular AOSs detected by means of a fluorescent probe.

In conclusion, short chain (C9 and C10) unsaturated fatty hydroxyl-acid derivatives whish are non-fluorinated appear to be particularly effective as anti-radical cell protection.

Study of the Anti-radical Effect, Analysis of Lipid Peroxidation.

Moreover, in the course of normal cell metabolism, during occasional exposure of the skin to stressful agents or in the course of dermatological diseases, reactive oxygenated species called Oxygenated Free Radicals (OFRs) are produced (Y. M. W. Janssen et al, 1993). OFRs, described as highly reactive metabolites, play an important role in a large number of processes such as inflammation, ageing and tumours.

OFRs are considered to be secondary messengers in cell signalling processes relating to oxidative stress and therefore as precocious mediators of the inflammatory process (A. Van Der Vliet and A. Bast. 1992)

Overproduction of OFRs leads to considerable damage in the cell. Certain cell constituents are therefore major targets of oxidative stress: lipid constituents of the plasma membrane (lipoperoxidation), proteins (denaturation and degradation) and genetic material or DNA (mutations) can undergo alterations. Cells are capable of limiting oxidative damage through various anti-radical defence systems (enzymatic and non-enzymatic antioxidants) (B. P. Yu, 1994; H. Steiling et al, 1999).

Nevertheless, under certain conditions, OFRs are produced in quantities such that cellular antioxidant activity is inadequate. These OFRs therefore become factors which trigger inflammatory disorders and tissue ageing (Y. Miyachi et al, 1986; M. Kress et al, 1995).

In order to evaluate the anti-radical activity of various hydroxylated derivatives according to the invention, we analysed their ability to provide protection against cell membrane changes triggered by oxidative stress (chemical) compared to a reference antioxidant (vitamin E).

The plasma membrane constitutes the main and initial target of OFRs which being rich in lipids is a site of increased peroxidation (A. W. Girotti, 1985). The peroxides generated in the course of this lipid oxidation process are also highly reactive and capable of breaking down protein and genetic material.

In order to evaluate membrane changes, we measured lipid peroxidation by in vitro assay of complexes between the products of lipid oxidation and thiobarbituric acid. These complexes are called TBARS (thiobarbituric acid reactive substances) and give the test its name: TBARS Test.

In order to mimic chemical oxidative stress, we treated a fibroblast line (L929) with a complex consisting of hydrogen peroxide ($H_2O_2$) and iron ($Fe^{2+}/Fe^{3+}$) thus reconstituting the Fenton reaction which is the source of oxygenated free radicals and particularly the hydroxyl radical (OH°) (D. A Vessey et al. 1992):

$$H_2O_2 + Fe^{2+} \rightarrow OH° + OH^- + Fe^{3+}$$

The products were evaluated on a murin fibroblast line L929. Cells were pretreated with different concentrations of the product for 16 hours and were then stimulated with the $H_2O_2/Fe^{2+}/Fe^{3+}$ complex (200 μM–1 mM) for 1 hour.

Stock solutions: 100 mg/ml ethanol, 4° C.

Final solutions: 0.02 ng/ml.

Peroxidation of membrane lipids was analysed by measuring TBARS (Protocol ref. PLN°2, according to Morliere et al, 1991).

Principle of the Test.

In an acid medium at 95° C., TBARS complexes are formed (thiobarbituric acid reactive substance) between the products of lipid oxidation (malondialdehyde or MDA) and thiobarbituric acid (TBA) which can be assayed using fluorescence compared to a standard MDA range. TBARS assays are therefore expressed in pmole/μg of protein. Proteins and TBARS are assayed in the intracellular medium.

Calculation of Percentage Protection of Cell Membranes:

Using the TBARS calculation in pmole/μg protein, we calculated the protective efficacy of various products against the oxidation of lipid membranes.

$$\% \text{ protection} = \frac{[TBAR \text{ control}] - [TBARS(+\text{products})]}{TBARS \text{ control}} \times 100$$

Four separate experiments were carried out. Several compounds were evaluated in the course of these experiments (the test only allows 10 molecules to be evaluated at one time). The compounds were evaluated several times and were chosen as a function of the results obtained in another test which also measured anti-radical activity (assay test for activated oxygen species).

The model used in this experiment (Fenton reaction) triggers considerable lipid peroxidation of the L929 fibroblasts. This massive release of the hydroxyl radical OH° thus generates oxidative stress in the cells, particularly in the membranes. However, in this type of oxidative reaction, the products resulting from lipid peroxidation are internalized in the cells and TBARS are therefore assayed in the intracellular medium.

Vitamin E at 400 μg/ml reduces lipid peroxidation triggered by the $H_2O_2/Fe^{2+}/Fe^{3+}$ complex and protects cell membranes very effectively.

The results of four experiments are presented in Table II.

It is very clear that these hydroxylated derivatives have stable and reproducible antioxidant activity. This is particularly true of derivatives with a short carbon chain.

TABLE II protection of membrane lipids by various hydroxylated derivatives.

| | | | | % membrane lipid protection | | |
|---|---|---|---|---|---|---|
| Molecules tested | | | | Experiment no. | Mean | Standard deviation |
| Vit E 400 μg/ml | | | | 4 | 44.66 | 25.85 |
| Compound of formula I | | | | | | |
| N | R | R | R | | | |
| 6 | H | H | H | 3 | 52.91 | 8.81 |
| 6 | H | H | F | 3 | 40.65 | 16.83 |
| 4 | H | H | F | 3 | 36.54 | 41.69 |
| 13 | H | H | H | 1 | 22.10 | |
| 3 | H | H | F | 1 | 38.14 | |
| 13 | H | H | F | 3 | 7.39 | 16.23 |
| 10 | H | H | H | 1 | 27.18 | |
| 4 | H | $CH_3$ | H | 2 | 57.75 | 3.15 |
| 10 | H | H | F | 3 | 13.13 | 13.37 |
| 14 | H | H | F | 1 | 35.30 | |
| 4 | H | H | H | 2 | 37.88 | 26.28 |
| 9 | H | H | H | 3 | 8.72 | 48.78 |
| 3 | H | H | H | 2 | 15.7 | 29.93 |

The in vitro model presented in this study reflects the consequences of major oxidative stress on the main cell target which is the plasma membrane. Lipid peroxidation assays therefore constitute a good marker of oxidative stress and make it possible to evaluate the antioxidant action of active ingredients against hydroxyl radicals in the cell membrane.

Vitamin E, an antioxidant molecule, makes it possible to validate this model with regard to effective protection of cell membranes against oxidative stress.

Keratinocyte Differentiation.

Finally, the epidermis is involved in the skin's main function which is that of resisting the environment and providing protection against it. It is a stratified and squamous epithelium that is constantly renewed. Homeostasis and tissue regeneration are based on keratinocyte cells, support cells, soluble factors, with cell proximity enhancing intercellular interactions and interactions with the extra-cellular matrix.

The stratum corneum, the final stage in epidermal differentiation, results from three major processes: the formation of keratin filaments, keratinocyte cornification and formation of the intercellular lipid cement organized in lamellar structures.

Within the epidermis, the composition and nature of lipids varies as a function of the differentiation status of the keratinocytes. Therefore as the basal cells transit towards cells in the horny layer, there is a substantial reduction in phospholipids which, in the living layers, are responsible for the intactness of plasma membranes. In parallel, there is an increase in neutral lipids (free fatty acids and triglycerides) and sterols (cholesterol) as well as a large increase in sphingolipids, particularly the ceramides. In the horny layer, we find 40-50% sphingolipids, 20-27% cholesterol and 9-26% free fatty acids. The ceramides are covalently bound to the glutamic residues of involucrine, a precursor of the corneal envelope. As a result of their hydrophobic nature, fatty acids are involved in controlling skin impermeability while cholesterol is involved in membrane fluidity.

Many specific proteins of the horny layer or stratum corneum (the layer which confers the barrier function on the epidermis) are produced in the granular layer consisting of the final keratinocytes to present transcription and translation activity prior to the nuclear lysis which accompanies cornification.

Keratinocyte differentiation is based mainly on the evolution of structural proteins such as keratin which contribute to the architectural intactness of the epidermis. Their expression varies as a function of the degree of maturity of epidermal cells. The superbasal layers contain basic keratin 1 and acid keratin 10, so-called terminal differentiation keratins.

Next to the horny layer, keratins interact with histidine rich proteins to form a relatively homogeneous mixture which fills the corneocytes. These proteins derive from a precursor, profilaggrin, which is a large molecule (MW>450 kDa) stored in the granular layer. This is a protein whose terminal N and C groups bind to calcium and therefore lead to dephosphorylation and partial proteolysis to generate filaggrin. This catalyses the formation of disulphide bridges between the keratin filaments and contributes to their incorporation into the corneocyte matrix. Moreover, as a result of proteolysis, this results in the production of amino acids and peptide derivatives which confer water retention properties on the horny layer.

The corneocytes in the horny layer essentially contain keratin filaments inserted into a dense matrix which is surrounded by a thick and resistant protein wall: the corneal envelope. Precursor proteins of this structure, arranged on the inner side of the plasma membrane are synthesized by the keratinocytes from the spiny layer. However, bridge formation, under the action of enzymes (transglutaminases), takes place between the spiny and granular layers. Many cytosolic proteins, combined with the membrane fraction of the keratinocytes or stored in the keratohyalin granules contribute to development of the corneal layer. We therefore note involucrine (68 kDa) which is rich in glutamine and lysine.

The impermeability of the horny layer is due in large part to the hydrophobic intercellular lipid cement which binds together the corneocytes. The lipid content of the epidermis is the final outcome of keratinocyte and sebaceous lipogenesis. In normal epidermis, a mixture of neutral and polar lipids is predominant in the deep layer and is gradually replaced by a more apolar content including the ceramides. Many proteins are involved in the lipogenesis process and therefore in the synthesis of ceramides. Amongst these, protein DES2 (sphingolipid C4-hydroxylase/delta-4 desaturase) has been detected. This has hydroceramide hydroxylase activity and is involved in the synthesis of phytoceramides. Its expression is induced by differentiation (MIZUTANI Y. et Al, 2004). Lipids synthesized by the keratinocytes are directed towards the skin surface by the lamellar bodies (keratinosomes). These are secreted into the intercellular spaces and are arranged in the form of continuous sheets aligned in parallel to the cell membranes of the corneocytes. This lipid reorganization which takes place in the course of epidermal differentiation brings into play a number of lipid transporters from the ABC transporter family (Adenosine Triphosphate Binding Cassette transporter). Amongst these transporters, some are expressed as a result of keratinocyte differentiation (ABCB1, ABCC1, ABCC3, ABCC4 and ABCG1), others have their expression suppressed (ABCB9 and ABCD1) while others still undergo no regulation. The role of transporters whose expression is induced was studied: for example, ABCG1 is involved in translocation of cholesterol in the keratinocytes undergoing differentiation. The expression of some members of another category of transporters, the FATPs (Fatty Acid Transport Protein) such as FATP1, FATP3, FATP4 and FATP5, is induced in the course of keratinocyte differentiation. These transporters are thought to be involved in reorganization of the neutral lipid pool (KIELAR et Al, 2003).

Normal human keratinocytes (NHK) proliferate and differentiate in vitro, forming stratified layers which mimic the basal organisation of the skin. Extracellular calcium concentrations in excess of 0.1 mM initiate a cascade of genome and non-genome events which take the keratinocytes from a proliferative phase towards a differentiation phase. Keratinocyte differentiation can then be evaluated by studying the expression of several markers such as keratins 1 and 10, transglutaminase 1, desaturase DES2, involucrine, FATP4 and ABCG1 transporters. We therefore evaluated the effect of certain hydroxyalcene carboxylic acids in an in vitro culture model.

The study design can be illustrated as follows: differentiation of NHK in vitro and samples for analysis.

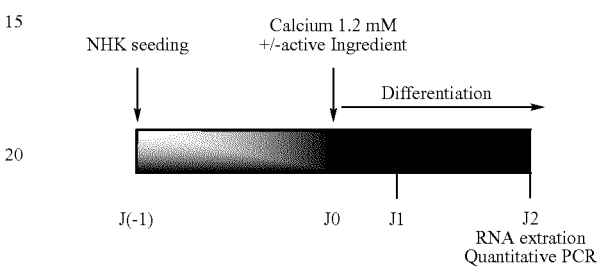

Culturing and Sampling Conditions.

Normal human keratinocytes are isolated from skin explants. They are cultured in KSFM medium (Gibco) with a low calcium content (0.1 mM) containing 25 µg/ml of BPE (bovine pituitary extract) and 1.5 mg/ml of EGF (epithelium growth factor). 24 hours after culturing, differentiation is triggered by the addition of calcium (final concentration 1.2 mM). The active ingredients are added or not at the same time as calcium at concentrations of 100 and 1 µg/ml in order to determine whether or not they have a potentialising effect on differentiation. Cells were then analysed 48 hours after the addition of calcium and these products.

Extraction of RNA and RT-PCR in Real Time.

Total RNA was extracted under cold conditions from keratinocytes.

After reverse transcription of mRNA into cDNA, PCRs were made up in 96 well plates (iCycler quantitative PCR apparatus, BioRad). Expression of transcripts of transglutaminase, desaturase (DES2), ABCG1 and FATP4 were standardized with respect to the expression of reference genes (GAPDH, UBC, HPRT). The level of expression of samples treated with calcium and the active ingredient were compared in terms of expression of samples treated only with calcium.

The results of the products at 1 µg/ml are given in the tables below:

| Compound of formula I | | | | Induction Factor vs Control (CaCl$_2$ 1.2 mM) | TG1 | DES2 | ABCG1 | FATP4 |
|---|---|---|---|---|---|---|---|---|
| n | R | R$_n$ | R$_1$ | | | | | |
| | H | H | F | Vit. D3 1 µM | 1.5 | 2.0 | 2.0 | 1.1 |
| 3 | H | H | F | | 1.5 | 1.7 | 1.5 | 1.2 |
| 3 | H | H | H | | 1.2 | 1.6 | 1.5 | 1.4 |
| 4 | H | H | F | | 1.6 | 2.2 | 2.6 | 1.3 |
| 4 | H | H | H | | 1.2 | 1.0 | 1.2 | 1.0 |
| 5 | H | H | H | | 1.5 | 1.8 | 2.7 | 1.0 |
| 6 | H | H | F | | 1.2 | 1.3 | 1.3 | 1.0 |
| 6 | H | H | H | | 1.1 | 1.7 | 1.9 | 1.2 |
| 9 | H | H | H | | 1.4 | 1.8 | 1.5 | 1.2 |
| 10 | H | H | F | | 1.4 | 1.6 | 1.4 | 1.0 |

-continued

| Compound of formula I | | | Induction Factor vs Control (CaCl$_2$ 1.2 mM) | TG1 | DES2 | ABCG1 | FATP4 |
|---|---|---|---|---|---|---|---|
| 10 | H | H | H | 1.5 | 2.0 | 1.4 | 1.2 |
| 13 | H | H | F | 4.2 | 9.0 | 4.8 | 2.2 |
| 13 | H | H | H | 1.4 | 3.0 | 3.0 | 1.4 |
| 14 | H | H | F | 1.7 | 2.8 | 4.0 | 1.0 |

At a dose of 1 μg/ml, the products have a moderate effect on the expression of differentiation markers.
Effects of products at 100 μg/ml.

| Compound of formula I | | | | Induction Factor vs Control (CaCl$_2$ 1.2 mM) | TG1 | DES2 | ABCG1 | FATP4 |
|---|---|---|---|---|---|---|---|---|
| N | R | R$_n$ | R$_1$ | Vit. D3 10 μM | 8.3 | 11.0 | 3.1 | 1.3 |
| 3 | H | H | F | | 0.9 | 1.9 | 1.2 | 1.2 |
| 3 | H | H | H | | 2.6 | 2.4 | 4.0 | 1.2 |
| 4 | H | H | F | | 1.7 | 3.2 | 2.6 | 1.4 |
| 4 | H | H | H | | 1.7 | 2.2 | 2.5 | 1.4 |
| 6 | H | H | F | | 7.8 | 10.3 | 6.3 | 1.9 |
| 6 | H | H | H | | 12.3 | 11.5 | 6.6 | 2.5 |
| 9 | H | H | H | | 14.8 | 51.7 | 13.8 | 4.5 |
| 10 | H | H | F | | 3.5 | 16.0 | 4.6 | 2.3 |
| 10 | H | H | H | | 31.4 | 125.8 | 25.5 | 5.9 |

Vitamin D3 at 10 μm induces the expression of transcripts of transglutaminase 1, DES2 and ABCG1 by a factor of 8.3, 11.1 and 3.1 respectively, compared to the control treated with calcium only. On the other hand, the expression of FATP4 is not altered by treatment with Vitamin D3.

The potentialising effect of differentiation has therefore been demonstrated with respect to the unsaturated fatty hydroxyl-acid derivatives of the invention.

Anti-inflammatory Effect Analysed in the Lipid Mediators of Inflammation.

In response to the many extracellular factors present in its environment, the keratinocyte which is the most abundant cell in the epidermis releases biologically active mediators, namely prostaglandins and leucotrienes which play an important role in the initiation and modulation of cutaneous inflammatory reaction and which are also involved in regulating the immune response. Prostaglandin PG6KF1alpha is a major metabolite produced by the stimulated keratinocyte and is representative of the modulation of metabolite production resulting from the metabolism of arachidonic acid resulting from the cyclo-oxygenase pathway.

Protocol:

A suspension of keratinocytes in DMEM 10% foetal calf serum was divided into 6 well plates (1.2. 106cells/wells) and incubated for 16 hours at 37° C. in a 5% CO$_2$ atmosphere. The keratinocytes were then rinsed with PBS in order to eliminate non adhering cells then exposed to the products to be tested included in DMEM without foetal calf serum (which could interfere with the assay).

The concentration tested in culture was 3 μg/ml. This was retained as the test concentration after a preliminary evaluation test for cytotoxicity (neutral red) and is not cytotoxic.

For each treatment, three wells were tested. Cells were pre-incubated for 60 minutes with the products to be tested then a stimulating agent was added to stimulate the arachidonic acid cascade (calcium ionophore) which was added for 5 hours: calcium ionophore A23187 was used at a concentration of 1 μm.

After 5 hours in culture, the culture medium for each well was recovered, centrifuged at 3000 rpm and stored at −80° C.

The production of prostaglandin 6KF1α for each of the tests was measured using a EUROMEDEX Elisa Kit.

Results:

Results are expressed as the percentage activity/stimulated control.

| Compound of formula I | | | | % inhibiting activity of evaluated molecules on the production of PG6KF1α Inflammation |
|---|---|---|---|---|
| N | R | Rn | R1 | 3 μg/ml |
| 3 | H | H | H | 29 |
| 4 | H | H | F | 30 |
| 4 | H | H | H | |
| 4 | H | CH$_3$ | H | |
| 8 | H | H | H | 32 |
| 8 | H | H | F | 44 |
| 9 | H | H | H | 31 |
| 10 | H | H | F | 18 |
| 10 | H | H | H | Non active |
| 13 | H | H | F | 14 |
| 13 | H | H | H | 25 |

Anti-inflammatory Properties: Inhibition of the Synthesis of Pro-Inflammatory Cytokine IL8.

The skin's barrier function provides protection against the external environment and keratinocytes in the epidermis can respond directly to a wide variety of irritants or allergenic agents and are actively involved in the cutaneous inflammatory and immune response process, particularly through the production of pro-inflammatory cytokines, mediators of protein origin. Amongst these biologically active molecules IL1α (Interleukin 1 α) and TNFα (Tumour Necrosis Factor α) are considered to be primary cytokines, as their release is enough to trigger inflammation since they induce adhesion molecules around the endothelial cells and their induction of chemotactic factors such as chemokines. The chemokine system controls leukocyte traffic in the course of the inflammatory response and is required for innate and adaptive immune response interactions.

In this study, we concentrated in particular on a chemokine (Interleukin 8) which is highly involved in the amplification of the inflammatory response and therefore whose principal role is to recruit and activate polynuclear neutrophils, namely by stimulating their release of pro-inflammatory molecules.

In this study, carried out using 96 well plates, we evaluated the activity of hydroxyl alkine acids on the production of Interleukin 8 produced in the keratinocytes by phorbol ester PMA and calcium ionophore A23187.

Protocol:

A suspension of keratinocytes in supplemented KSFM was divided between 96 well plates (3.10$^4$ cells/wells) and incubated for 16 hours at 37° C. under an atmosphere of 5% CO$_2$. The keratinocytes were then rinsed with PBS in order to eliminate non adhering cells then exposed to the products to be tested included in non supplemented KSFM (which could interfere with the assay).

The concentration tested in culture was 3 µg/ml. This was retained after a preliminary test to evaluate cytotoxicity (neutral red) and is not cytotoxic.

3 wells were used for each treatment. Cells were preincubated for 60 minutes with the products to be tested then stimulated, in parallel to negative controls without stimulant: Phorbol Myristate Acetate (PMA) 1 µm+Calcium ionophore (A23187) 0.1 µm.

Incubation for 6 hours at 37° C. in a humid air atmosphere containing 5% $CO_2$.

The culture medium for each of the wells was recovered, centrifuged at 3000 rpm and stored at −80° C.

Cytokine assay: IL8 was assayed using the ELISA kit immunoenzyme method (immunotech).

Results:
The results are given as percentage activity/stimulated control.

| Compound of formula I | | | % inhibitory activity of evaluated molecules on production of PG6KF1α Inflammation |
|---|---|---|---|
| n | R | $R_n$ | $R_1$ | 3 µg/ml |
| 3 | H | H | H | 50 |
| 4 | H | H | F | Non-active |
| 4 | H | H | H | 15 |
| 4 | H | $CH_3$ | H | Non-active |
| 6 | H | H | H | Not determined |
| 8 | H | H | H | Non-active |
| 8 | H | H | F | Non-active |
| 9 | H | H | H | 16 |
| 10 | H | H | F | 30 |
| 10 | H | H | H | 30 |
| 13 | H | H | F | 107 |
| 13 | H | H | H | 62 |
| 14 | H | H | H | Non-active |

The compounds according to the invention were evaluated in terms of anti-inflammatory activity on the release of Interleukin 8 by human keratinocytes NHK stimulated by phorbol ester PMA+calcium ionophore A23187.

Three separate experiments were performed: synthesis of the data obtained reveals the anti-inflammatory potential of the following 2 compounds in particular:
n=13, R=$R_n$=H, $R_1$=F
n=13, R=$R_n$=$R_1$=H For the concentration evaluated for each of the molecules and after calculation of the effective dose 50, our results show the following:

| Compound of formula I | | | | % Inhibition | |
|---|---|---|---|---|---|
| n | R | $R_n$ | $R_1$ | a 3 µg/ml | ED50 |
| 13 | H | H | F | 107 | <3 µg/ml |
| 13 | H | H | H | 62 | <3 µg/ml |

Inflammation and Pruritus: Analysis of Calcium Flux Following Stimulation of PAR2 Receptors.

The protease-activated receptor-2 (PAR-2) is involved in the physiopathology of several diseases where there is an inflammatory reaction. PAR-2 is expressed by different types of skin cells: keratinocytes, myoepithelial cells of the sweat glands, hair follicles, dendritic like cells of the dermis and endothelial cells of the lamina propria and dermis (Steinhoff et al. 1999; Santulli et al., 1995). The melanocytes do not express this receptor (Seiberg et al., 2000) although PAR-2 plays an important role in pigmentation by encouraging the transfer of melanin from the melanocytes to the keratinocytes (Sharlow et al., 2000).

The serine proteases generated by the epidermis exert chemotactic effects which induce the recruitment of leukocytes in the skin. These are also involved in the regulation of homeostasis, mitogenesis and epidermal differentiation and they modulate the skin's barrier function. In addition, the serine proteases contribute to the physiopathology of cutaneous diseases linked to inflammation, host defence, cancerogenesis, fibrosis and nerve stimulation.

The physiological and physiopathological cutaneous properties of the serine proteases are thought to be partially linked to the PAR receptors. In fact, the PAR-2 receptors are overexpressed in the epidermis, dermis and vessels in the case of inflammatory skin diseases such as atopic dermatitis, lichen planus and psoriasis (Steinhoff et al., 1999). The PAR2 receptors are also thought to play a role in the development of pruritus in patients with atopic dermatitis (Steinhoff et al., 2003).

Activation of PAR-2 by a trypsin like protease triggers the production of IL8 from the keratinocytes (HaCaT) (Hou et al., 1998). More recently, it has been demonstrated that IL-8, a chemo-attractive chemokine for leukocytes, allows the infiltration of neutrophils into the epidermis in patients with psoriasis vulgaris (Iwakiri et al., 2004).

Intracellular signalling of the PAR-2 receptor partially underlies mobilization of intra and extra cellular calcium.

We therefore considered evaluating anti-PAR-2 activity of hydroxyl acid derivatives of formula I on the influx of intracellular calcium induced after specific stimulation by PAR-2 receptors for trypsin present in human keratinocytes from the HaCaT line.

This technique is based on the use of an esterified fluorescent probe by an AM group which facilitates its penetration by passive diffusion into the cell. The probe used is Fluo-4/AM. Only the de-esterified form bound to the calcium ion is excitable in fluorescence (at 485 nm) and emits at 535 nm.

Percentage Inhibition of Calcium Flux Induced by Trypsin.

| | | % stimulation | Standard deviation | % inhibition |
|---|---|---|---|---|
| Without probe | | 3.82 | 0.79 | — |
| Trypsin 10 nM | | 13.67 | 3.14 | — |
| STI 1 µm | | 8.39 | 2.85 | 54 |
| R = $R_n$ = H | 0.1 µg/ml | 13.78 | 0.82 | −1 |
| $R_1$ = F | 0.3 µg/ml | 13.06 | 1.47 | 6 |
| n = 13 | 1 µg/ml | 12.74 | 1.25 | 9 |
| | 3 µg/ml | 12.97 | 0.92 | 7 |
| | 10 µg/ml | 9.55 | 1.96 | 42 |
| R = $R_n$ = $R_1$ = H | 10 µg/ml | 15.33 | 3.00 | −17 |
| n = 10 | 30 µg/ml | 14.10 | 3.42 | −4 |
| | 100 µg/ml | 9.84 | 3.26 | 39 |
| R = $R_n$ = $R_1$ = H | 10 µg/ml | 14.68 | 2.56 | −10 |
| n = 14 | 30 µg/ml | 12.90 | 3.58 | 8 |
| | 100 µg/ml | 11.37 | 2.62 | 23 |

Stimulation by Trypsin

On keratinocytes originating from line HaCaT:

The hydroxy acid derivatives of general formula I mentioned in the table above have an inhibitory effect on calcium flow induced by trypsin at a concentration of 10 µg/ml for the former and at a concentration of 100 µg/ml for the following two compounds.

In vitro, at the cell level, specific stimulation of the PAR-2 receptors by trypsin leads to mobilisation of intra and extracellular calcium detected with the aid of the fluorescent probe.

Under the conditions of the experiment and at the concentrations tested, the compounds of general formula (I) mentioned in the table above significantly modulate the activity of anti-PAR-2.

Effects of Fatty Hydroxy Acid Derivatives on Melanin Synthesis In Vitro

The melanocytes are star-shaped cells found in small amounts in the basal layer of the epidermis. Their main role is to carry out melanogenesis, the process by means of which melanin is synthesized in specialized organelles, the melanosomes, after which is it transported and distributed to the neighbouring keratinocytes via their dendrites. This contact with the keratinocytes leads to skin pigmentation, the mechanism which protects the epidermis against the mutagenic effects of ultraviolet rays. Each melanocyte is in contact with around 36 keratinocytes, thus forming an "epidermal melanisation unit".

Melanogenesis consists of a series of enzyme and spontaneous reactions for which the precursor is tyrosine. Three main enzymes are involved in this process: tyrosinase, and tyrosinase-related protein 1 and 2 (TRP1 and 2) (1). Tyrosinase catalyses the transformation of tyrosine into dopaquinone. After this, there are two possible synthesis pathways eumelanogenesis and pheomelanogenesis. The conversion of dopaquinone into eumelanin takes place through a series of successive oxidation reactions involving TRP-1 and TRP-2. Eumelanin corresponds to a brown-black pigment with a low sulphur content and provides photoprotection. In pheomelanogenesis, molecules with a high sulphur content are incorporated into dopaquinone to give pheomelanin, the yellow-orange in colour found in red-heads.

The physiological stimulus for melanin synthesis is the sun which leads to an increased number of melanocytes, neosynthesis of melanin and morphological changes in the melanocytes combining increased dendricity with increased transfer of the melanosomes to the keratinocytes. At the molecular level, exposure to the sun stimulates the synthesis and secretion of alpha melanocyte stimulating hormone. α-MSH increases intramelanocyte cAMP concentration, activating a transcription factor, Mitf, which in its turn stimulates the transcription activity of the genes coding for tyrosinase, TRP-1 and TRP-2.

Some exogenous molecules are also known to have a negative regulation effect on melanogenesis. Hydroquinone inhibits the synthesis of melanin by presenting itself as a substrate for tyrosinase in order to divert its activity.

The modulating effect of unsaturated fatty hydroxy acid derivatives on melanogenesis was analysed. To do this, measurement of melanin synthesis by colorimetric assay was performed on a murine melanome cell line: line B16-F10.

The effect of products was investigated in a basal situation and after stimulation by α-MSH in order to determine depigmenting capacity.

Melanin Assay

Levels of extracellular and intracellular melanin were measured by spectrophotometry at a wavelength of 405 nm according to the protocol described by Anob et al., 1999. The amount of pigment was determined using a standard melanin range and analysis on Microwin software (Berthold Biotechnologies). A total protein assay was carried out for intracellular melanin samples by means of the BCA-Copper method at 540 nm. The standard range was made up using standard protein BSA (Bovine Serum Albumin).

Results

In the basal situation, alpha MSH at 1 µM increases the production of melanin by 100% compared to the control cells.

This increase in melanin is countered by depigmentation agents such as hydroquinone at 1 µg/ml or vitamin C at 40 µg/ml which lead to 60% inhibition of alpha MSH activity.

In the basal situation at 30 µg/ml:

The compound of general formula I with n=10, R=$R_n$=H, $R_1$=F inhibits melanin synthesis by 30 to 45% whereas in the absence of alpha MSH, this same compound at 30 µg/ml leads to 45 to 60% inhibition.

The compound of general formula I with n=10, R=$R_1$=$R_n$=H at 30 µg/ml shows lower activity than the preceding compound, 15% inhibition in the basal situation whereas in the presence of alpha MSH, the inhibition potential of this compound towards this melanotropic substance is similar to that of the preceding compound, in other words 45 to 60%.

At 10 µg/ml, the inhibitory activity of these 2 acids on the induction of melanogenesis by alpha MSH is in the order of 35%.

The invention claim is:

1. Unsaturated fatty hydroxy acid derivatives corresponding to general formula (I):

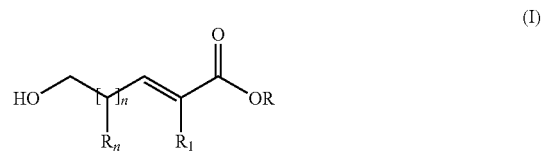

in which:

$R_n$ independently represents one or other of H or a linear or branched alkyl group consisting of 1 to 6 carbon atoms, optionally substituted by a halogen atom, $R_1$ represents H, F, Cl, Br, or $CF_3$, R represents H, and $3 \leq n \leq 14$, on the condition, however, that when n≠10, at least one of the $R_1$ radicals and $R_n$ radicals does not represent hydrogen.

2. Unsaturated fatty hydroxy acid derivatives of general formula (I) according to claim 1 wherein:

$R_1$ represents F, Cl, Br or $CF_3$, and

R, $R_n$ and n have the definitions recited in claim 1.

3. Unsaturated fatty hydroxy acid derivatives of general formula (I) according to claim 1 wherein:

R, $R_1$ and $R_n$ have the meanings recited in claims 1, and $6 \leq n \leq 14$, on the condition, however, that when n≠10, at least one of the $R_1$ radicals and $R_n$ radicals does not represent hydrogen.

4. Unsaturated fatty hydroxy acid derivatives of general formula (I) according to claim 1 wherein:

$R_1$ represents F, Cl, Br or $CF_3$, and $R_n$ represents hydrogen.

5. Unsaturated fatty hydroxy acid derivatives of general formula (I) according to claim 1 wherein:

$R_1$ represents F, Cl, Br or $CF_3$, and at least one of the $R_n$ radicals represents a linear or branched alkyl group consisting of 1 to 6 carbon atoms, optionally substituted by a halogen atom.

6. Unsaturated fatty hydroxy acid derivatives of general formula (I) according to claim 1 wherein:

$R_1$ represents fluorine, and
$R_n$ represents hydrogen.

7. Unsaturated fatty hydroxy acid derivatives of general formula (I) according to claim 6 wherein:

$R_1$ represents fluorine,
$R_n$ represents hydrogen and
n=13.

8. Unsaturated fatty hydroxy acid derivatives of general formula (I) according to claim 2 wherein:

$R_1$ represents fluorine,
$R_n$ represents hydrogen, and
n=6.

9. Unsaturated fatty hydroxy acid derivatives of general formula (I) according to claim 1 wherein:

R and $R_1$ represent hydrogen,
only one of the $R_n$ radicals represents a methyl group, the others being hydrogen atoms, and
n=4.

10. Unsaturated fatty hydroxy acid derivatives of general formula (I) according to claim 1 wherein:

$R_1$ and $R_n$ represent hydrogen, and
n=10.

11. Unsaturated fatty hydroxy acid derivatives of general formula (I) according to claim 2 wherein:

$R_1$ represents fluorine,
$R_n$ represents hydrogen, and
n=10.

12. Unsaturated fatty hydroxy acid derivatives of general formula (I) according to claim 2 wherein:

$R_1$ represents fluorine,
$R_n$ represents hydrogen, and
n=8.

13. Dermocosmetologic compositions including an unsaturated fatty hydroxy acid derivative of general formula (I) according to claim 1 combined with a dermatologically acceptable excipient.

14. A method for the treatment of keratinisation and/or for improving healing, and/or for manufacturing a dermocosmetologic composition with anti-radical, anti-inflammatory, anti-pruriginous activity, which comprises administering to a patient in need thereof an unsaturated fatty hydroxyl acid derivatives of general formula I

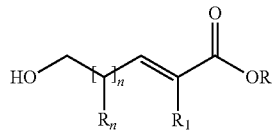

in which:

$R_n$, independently represents one or other H or a linear or branched alkyl group consisting of 1 to 6 carbon atoms, optionally substituted by a halogen atom, $R_1$ represents H, F, Cl, Br, or $CF_3$, R represents H or a linear or branched alkyl group with 1 to 6 carbon atoms, optionally substituted by a halogen atom, and $3 \leq n \leq 14$.

15. The method of claim 14 for the treatment of psoriasis, pruritus and/or atopic dermatitis.

16. A method for the treatment of skin aging and white or brown age spots which comprises administering to a patient in need thereof an unsaturated fatty hydroxyl acid derivative according to claim 1.

17. A method for whitening the skin which comprises administering to a patient in need thereof an unsaturated fatty hydroxyl acid derivative according to claim 1.

18. Unsaturated fatty hydroxy acid derivates of general formula (I) according to claim 1, wherein R and $R_n$ represent a linear or branched alkyl group consisting of 1 to 6 carbon atoms, substituted by fluorine.

19. Unsaturated fatty hydroxy acid derivates of general formula (I) according to claim 5, wherein the at least one of the $R_n$ radicals represent a linear or branched alkyl group consisting of 1 to 6 carbon atoms, substituted by fluorine.

20. Unsaturated fatty hydroxyl acid derivatives of general formula (I) according to claim 1 selected from the following compounds:

10-hydroxy-dec-2-fluro-2-enoic acid,
12-hydroxy-dodeca-2-fluoro-2t-enoic acid,
14-hydroxy-tetradec-2t-enoic acid,
14-hydroxy-tetradec-2-fluoro-2-enoic acid,
17-hydroxy-heptadec-2-fluoro-2-enoic acid.

21. A method for the treatment of pigmentation disorders which comprises administering to a patient in need thereof an unsaturated fatty hydroxyl acid derivative according to claim 1.

* * * * *